(12) United States Patent
Allard, III

(10) Patent No.: US 9,963,863 B2
(45) Date of Patent: May 8, 2018

(54) PLUMBING CONTROL SYSTEM, METHOD, AND APPARATUS AND PREVENTING REPEATED USE OF AN APPLIANCE WITH FEEDBACK

(71) Applicant: SDB IP Holdings, LLC, Oviedo, FL (US)

(72) Inventor: Rock R. Allard, III, Oviedo, FL (US)

(73) Assignee: SDB IP Holdings, LLC, Oviedo, FL (US)

( * ) Notice: Subject to any disclaimer, the term of this patent is extended or adjusted under 35 U.S.C. 154(b) by 20 days.

(21) Appl. No.: 15/259,723

(22) Filed: Sep. 8, 2016

(65) Prior Publication Data

US 2018/0066422 A1  Mar. 8, 2018

(51) Int. Cl.

| | | |
|---|---|---|
| *E03D 1/00* | (2006.01) | |
| *E03D 5/02* | (2006.01) | |
| *E03D 5/09* | (2006.01) | |
| *E03D 5/10* | (2006.01) | |
| *F16K 37/00* | (2006.01) | |
| *G08B 5/36* | (2006.01) | |
| *G08B 21/18* | (2006.01) | |

(52) U.S. Cl.
CPC ............ *E03D 5/026* (2013.01); *E03D 5/09* (2013.01); *E03D 5/105* (2013.01); *F16K 37/0025* (2013.01); *G08B 5/36* (2013.01); *G08B 21/182* (2013.01)

(58) Field of Classification Search
CPC .. E03D 4/026; E03D 4/09; E03D 4/10; F16K 37/0025

USPC ............................................................ 4/314
See application file for complete search history.

(56) References Cited

U.S. PATENT DOCUMENTS

| | | | |
|---|---|---|---|
| 4,471,498 A | 9/1984 | Robertshaw | |
| 4,985,944 A | 1/1991 | Shaw | |
| 5,235,706 A | 8/1993 | Allen et al. | |
| 5,438,714 A * | 8/1995 | Shaw | E03B 7/04 137/357 |
| 5,771,501 A | 6/1998 | Shaw | |
| 6,477,718 B1 * | 11/2002 | Wang | A47K 17/00 4/300 |
| 6,769,443 B2 | 8/2004 | Bush | |

(Continued)

FOREIGN PATENT DOCUMENTS

WO   2015095505 A1   6/2015

*Primary Examiner* — Huyen Le
(74) *Attorney, Agent, or Firm* — The Webb Law Firm

(57) ABSTRACT

Provided is a system, method, and apparatus for preventing repeated use of a restroom appliance with visual feedback. The system includes a valve configured to control flow of a fluid by at least one valve operation, an actuator configured to request a use of the restroom appliance, at least one indicator configured to display at least three different visual states, and at least one controller in communication with the actuator, the valve, and the at least one indicator. The at least one controller is programmed or configured to control the at least one indicator to display a first visual state, receive a plurality of requests to operate the restroom appliance exceeding a maximum number of valve operations, perform a first valve operation in response to receiving a first request, and control the at least one indicator to display a second visual state in response to performing the first valve operation.

25 Claims, 5 Drawing Sheets

(56) References Cited

U.S. PATENT DOCUMENTS

| | | | |
|---|---|---|---|
| 6,779,206 B1 * | 8/2004 | Sykes | A47K 17/00 4/301 |
| 8,984,675 B2 * | 3/2015 | Miller | E03F 1/006 4/313 |
| 2008/0087856 A1 | 4/2008 | Wilson et al. | |

* cited by examiner

PLUMBING CONTROL SYSTEM, METHOD, AND APPARATUS AND PREVENTING REPEATED USE OF AN APPLIANCE WITH FEEDBACK

BACKGROUND OF THE INVENTION

Field of the Invention

This invention relates generally to restroom appliances and valves and, in particular, to a system, method, and apparatus for preventing repeated use of a restroom appliance through visual feedback.

Technical Considerations

Fluid control systems are used to manage and regulate the flow of fluid through plumbing systems, allowing and preventing fluid flow to and through various plumbing fixtures. For example, control systems are used to regulate flow through toilets and lavatories in a facility, such as a prison. Prior art plumbing control systems include a plurality of toilets and lavatories within a facility, each of which are integrated through an associated controller, which, in turn, communicates with a central controller. Also, each toilet and lavatory typically include a solenoid valve to operate the fixture based on use of an actuator. The control system uses the central controller to receive requests from any individual fixture, process the request, and communicate an appropriate signal back to the logic circuit or controller associated with each fixture, either allowing or disallowing fluid flow through a flow valve.

In certain facilities and institutions, such as prisons, these plumbing control systems can be used to delay operation of a single fixture, e.g., a flush valve for a toilet, within the facility, and/or to prevent such a fixture from being operated more than a specified number of times within a predetermined time period, thereby preventing flooding of the toilet. These systems are classified as "delay" and/or "lockout" systems. For example, U.S. Pat. No. 4,985,944 to Shaw is directed to a plumbing control system and method for prisons, which causes operation of a valve to be delayed for a selected period after the sensor has been operated and limits the number of operations of the valve per unit time. Thus, a user is prevented from utilizing the fixture in a quick and successive manner, which could overload the fluid system. Another example of a plumbing control system which delays operation of the valve is described in U.S. Pat. No. 5,771,501 to Shaw. U.S. Pat. No. 6,769,443 to Bush, the entirety of which is hereby incorporated by reference, describes a control system that protects against repeated use of a fixture, overload of the fixture, and overload of the system, and tracks and warns the controller of these repeated uses.

The users of the restroom appliances including fixtures having such "delay" and/or "lockout" features may not be aware of previous uses by others and, as a result, may not be aware if the restroom appliance is currently usable or locked out, if the next usage of the restroom appliance will create a lockout, or if the restroom appliance has been reset and is capable of more than a single usage during a time period. For example, in a prison or other institutional environment in which it is desirable to manage and limit the usage of restroom appliances, one restroom appliance may be shared by multiple individuals. Thus, if the usage of a restroom appliance is limited to a predetermined number of uses in a time period, a subsequent user may be unaware of whether the restroom appliance can be used or, if it can be used, how many additional times it can be used before it is placed in a "lockout" mode. As an example, if a first inmate uses a toilet and flushes twice, and the maximum number of flushes within a time period is three, a second inmate may approach the toilet within the time period thinking that three flushes are available. However, since the previous inmate flushed twice and the time period has not elapsed, the second inmate may unknowingly only have one flush available before the valve prevents any further usage. In this situation, if the second inmate flushes before or during his usage of the toilet, the unavailability of an additional flush may result in waste being left in the toilet bowl.

Therefore, it would be advantageous to provide a system, method, and apparatus for preventing repeated use of a restroom appliance that overcomes some or all of the problems associated with the prior art.

SUMMARY OF THE INVENTION

It is an object of the invention to provide a system, method, and apparatus for preventing repeated use of a restroom appliance with visual feedback that overcomes the above-described deficiencies of the prior art.

According to a non-limiting embodiment of the present invention, provided is a system for preventing repeated use of a restroom appliance with visual feedback, including: a valve configured to control flow of a fluid to a restroom appliance by at least one valve operation; an actuator configured to request a use of the restroom appliance; at least one indicator configured to display at least three different visual states; at least one controller in communication with the actuator, the valve, and the at least one indicator, the at least one controller programmed or configured to: control the at least one indicator to display a first visual state of the at least three different visual states; receive, from the actuator during a first time period, a plurality of requests to operate the restroom appliance, the plurality of requests exceeding a maximum number of valve operations associated with the first time period; perform a first valve operation in response to receiving a first request of the plurality of requests; control the at least one indicator to display a second visual state of the at least three different visual states in response to performing the first valve operation or receiving the first request; perform at least one subsequent valve operation in response to receiving a subsequent request of the plurality of requests, the subsequent request corresponding to the maximum number of valve operations; control the at least one indicator to display a third visual state of the at least three different visual states in response to performing the at least one subsequent valve operation or receiving the at least one subsequent request; and prevent additional valve operations by request of the actuator during a remainder of the first time period and/or for a second time period in response to performing the at least one subsequent valve operation or receiving the at least one subsequent request.

In non-limiting embodiments, the at least one controller may be further programmed or configured to control the at least one indicator to display the first visual state of the at least three different visual states in response to determining that the first time period and/or the second time period has elapsed.

In non-limiting embodiments, the actuator may comprise a button comprising the at least one indicator, the at least one indicator configured to display at least two different colored lights. Further, the actuator may also comprise a button comprising the at least one indicator, the at least one indicator arranged as a ring surrounding the button. The actuator may comprise at least one of the following: an infrared sensor, a proximity sensor, a push button, a capacitance sensor, a lever, or any combination thereof.

In non-limiting embodiments, the first visual state is a steady light, wherein the second visual state is a flashing light, and wherein the third visual state is a steady or flashing light of a different color than the first visual state. In some embodiments, the second state may comprise a light pattern indicating a number of uses that have taken place or a number of valve operations that are left within the first time period. Further, the light pattern may comprise flashing a light a number of times corresponding to the number of valve operations that are left within the first time period.

In non-limiting embodiments, the maximum number of valve operations may be three and the first time period may be about five minutes. Further, additional valve operations by request of the actuator may be prevented for a second time period in response to performing the at least one subsequent valve operation or receiving the at least one subsequent request, the second time period comprising a lockout period. In some embodiments, additional valve operations by request of the actuator may be prevented for a remaining duration of the first time period in response to performing the at least one subsequent valve operation or receiving the at least one subsequent request.

In non-limiting embodiments, the valve operation comprises at least one of the following: a flush of a flush valve, opening a faucet valve for a predetermined time period, or opening a shower valve for a predetermined time period.

According to another non-limiting embodiment of the present invention, provided is a method for preventing repeated use of a restroom appliance with visual feedback, the restroom appliance comprising a valve and an actuator configured to cause an operation of the valve, the method including: controlling at least one indicator to display a first visual state of the at least three different visual states; receiving, from the actuator during a first time period, a plurality of requests to operate the restroom appliance, the plurality of requests exceeding a maximum number of valve operations associated with the first time period; performing a first valve operation in response to receiving a first request of the plurality of requests; controlling the at least one indicator to display a second visual state of the at least three different visual states in response to performing the first valve operation or receiving the first request; performing at least one subsequent valve operation in response to receiving a subsequent request of the plurality of requests, the subsequent request corresponding to the maximum number of valve operations; controlling the at least one indicator to display a third visual state of the at least three different visual states in response to performing the at least one subsequent valve operation or receiving the at least one subsequent request; and preventing additional valve operations by request of the actuator during a remainder of the first time period and/or for a second time period in response to performing the at least one subsequent valve operation or receiving the at least one subsequent request.

According to a further preferred and non-limiting embodiment, provided is an apparatus for preventing a user from repeatedly using a restroom appliance, the restroom appliance including a valve and an actuator configured to cause an operation of the valve, the apparatus including at least one controller in communication with the valve and the actuator, the at least one controller programmed or configured to: control at least one indicator to display a first visual state of the at least three different visual states; receive, from the actuator during a first time period, a plurality of requests to operate the restroom appliance, the plurality of requests exceeding a maximum number of valve operations associated with the first time period; perform a first valve operation in response to receiving a first request of the plurality of requests; control the at least one indicator to display a second visual state of the at least three different visual states in response to performing the first valve operation or receiving the first request; perform at least one subsequent valve operation in response to receiving a subsequent request of the plurality of requests, the subsequent request corresponding to the maximum number of valve operations; control the at least one indicator to display a third visual state of the at least three different visual states in response to performing the at least one subsequent valve operation or receiving the at least one subsequent request; and prevent additional valve operations by request of the actuator during the first time period and/or for a second time period in response to performing the at least one subsequent valve operation or receiving the at least one subsequent request.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

BRIEF DESCRIPTION OF THE DRAWINGS

Additional advantages and details of the invention are explained in greater detail below with reference to the exemplary embodiments that are illustrated in the accompanying schematic figures, in which.

DESCRIPTION OF THE PREFERRED EMBODIMENTS

Figure 1:
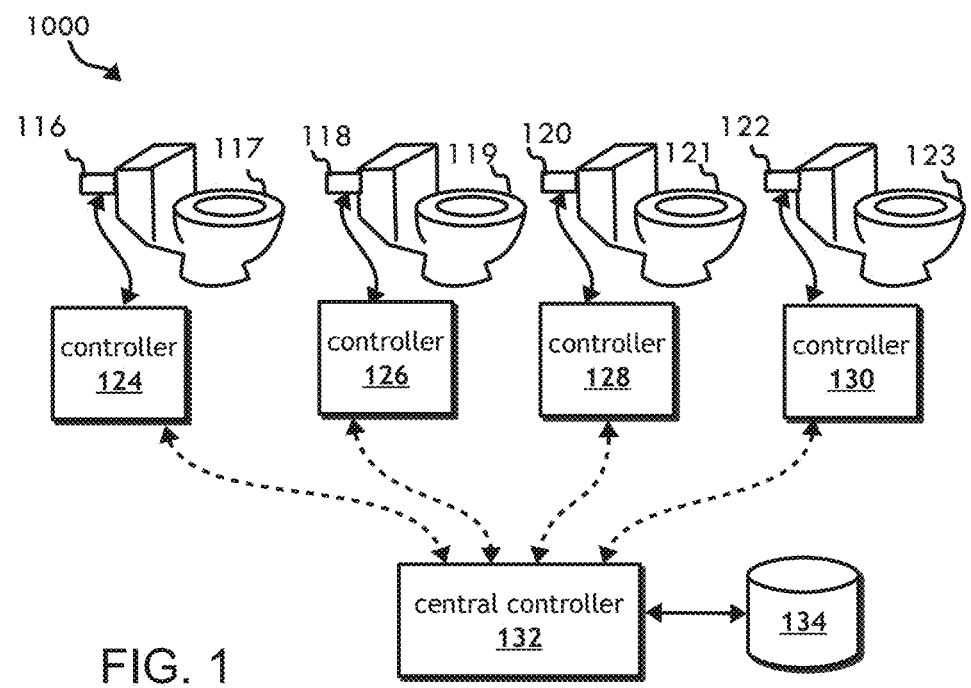
FIG. 1 is a schematic diagram for a system for preventing repeated use of a restroom appliance with visual feedback according to the principles of the present invention.

As used herein, spatial or directional terms, such as "up," "down," "above," "below," "top," "bottom," and the like, relate to the invention as it is shown in the drawing figures. However, it is to be understood that the invention can assume various alternative orientations and, accordingly, such terms are not to be considered as limiting. Further, all numbers expressing dimensions, physical characteristics, processing parameters, and the like used in the specification and claims are to be understood as being modified in all instances by the term "about". Accordingly, unless indicated to the contrary, the numerical values set forth in the following specification and claims are approximations that can vary depending upon the desired properties sought to be obtained by the present invention. At the very least, each numerical value should be considered in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, and/or routed between the first and second unit or component. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

In a preferred and non-limiting embodiment, provided is a system, method, and apparatus for preventing repeated use of a restroom appliance with visual feedback. A restroom appliance, such as a toilet, shower, faucet, and/or the like, includes a plumbing fixture, such as a valve, configured to control flow of a fluid to, from, and/or within the restroom appliance. The valve controls the flow of fluid through at least one valve operation, which may include opening the valve, closing the valve, restricting the flow of fluid through the valve, and/or the like, using a solenoid or any other like mechanism. A controller is configured to prevent a user of the restroom appliance from overloading the plumbing system and/or overusing the restroom appliance by limiting usage of the restroom appliance to a predetermined number of uses within a time period. An indicator configured to display a plurality of different visual states provides a user with a current status of the restroom appliance, such as whether it is available for full usage (e.g., the predetermined number of uses are all available), available for limited usage (e.g., less than the predetermined number of uses are left within a time period), or "locked out" and unavailable for any further uses for a time period.

It will be appreciated that various types of restroom appliances may be used in connection with the present invention. The term restroom appliance, as used herein, refers to any type of appliance that is provided with fluid via one or more valves. A restroom appliance may include, for example, a toilet, faucet, shower, and/or the like. A valve, as used herein, refers to any type of valve capable of providing, controlling, and/or restricting the flow of a fluid to, from, and/or within a restroom appliance. As an example, a valve may include a flush valve for a toilet, a shower valve for a shower, a faucet valve for a faucet, or any other type of mechanism for providing, controlling, and/or restricting fluid flow. In preferred and non-limiting examples, a valve includes a solenoid that operates the valve to open, close, and/or restrict the flow of water in response to one or more commands received from a controller. Those skilled in the art will appreciate that other arrangements are possible.

Referring now to FIG. 1, a system 1000 for preventing repeated use of a restroom appliance with visual feedback is shown according to a preferred and non-limiting embodiment. The system 1000 includes restroom appliances 117, 119, 121, 123 each having a respective valve 116, 118, 120, 122 and a respective controller 124, 126, 128, 130. It will appreciated that each controller may also control one or more valves of other plumbing appliances and that, in some examples, a single controller may be used. The controllers 124, 126, 128, 130 may be located directly on the valves 116, 118, 120, 122 or at some other location (e.g., in a chase area, behind an appliance or wall, and/or the like). In the illustrated non-limiting embodiment, the controllers 124, 126, 128, 130 for each respective valve are in communication with a central controller 132. However, it will be appreciated that a central controller 132 or a single local controller may be used instead of each of the respective controllers 124, 126, 128, 130 and that, in some examples, a central controller 132 may not be used. Moreover, the controllers 124, 126, 128, 130 may have stored thereon, or be in communication with, program instructions that, when executed by a controller, cause the controller to perform data processing tasks. For example, a computer-readable medium may be memory located on or in communication with a controller for storing the program instructions.

The term controller, as used herein, refers to one or more of any type of processor, microprocessor, computer system, logic circuit, and/or other like data processing devices. Further, the term controller, unless noted otherwise, may refer to one or more controllers that are local to a specific restroom appliance, local to a plurality of restroom appliances or facility, and/or remote from the restroom appliances or facility. For example, a controller may be incorporated into a valve or restroom appliance, separate from a valve or restroom appliance, and/or arranged as a central controller that communicates with controllers local to the valves and restroom appliances. Various other arrangements are possible.

With continued reference to FIG. 1, the central controller 132 is in communication with a data storage device 134 to store usage data concerning the restroom appliances 117, 119, 121, 123 and/or the associated valves 116, 118, 120, 122. Each restroom appliance 117, 119, 121, 123, valve 116, 118, 120, 122, and/or the associated controllers 124, 126, 128, 130 may also include a data storage device, such as memory, to store usage data. Usage data may include, for example, a counter representing a number of times that a particular restroom appliance has been used and/or a number of valve operations performed by a particular valve. Usage data may be specific to a time period, e.g., a number of uses within a specified time period, and/or may represent an aggregate number of uses.

Figure 2:
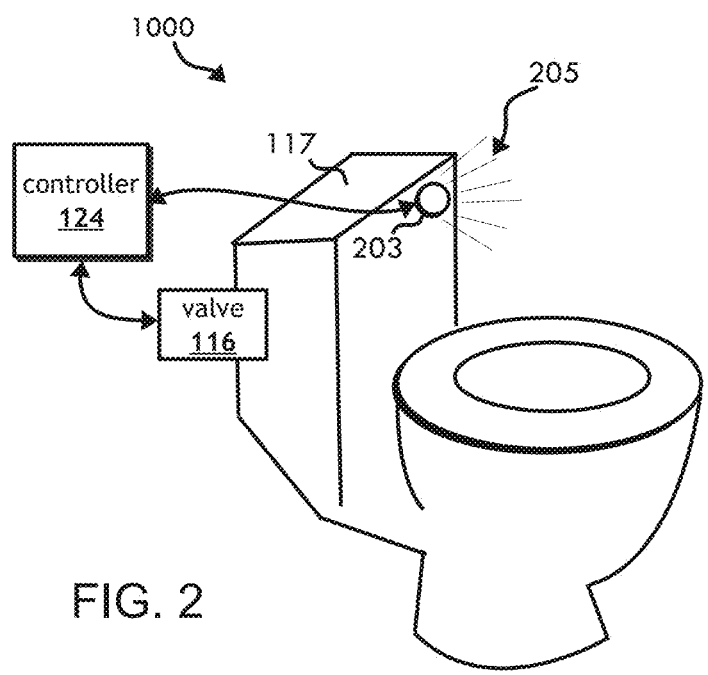
FIG. 2 is a further schematic diagram for a system for preventing repeated use of a restroom appliance with visual feedback according to the principles of the present invention.

Referring now to FIG. 2, a system 1000 for preventing repeated use of a restroom appliance with visual feedback is shown according to a preferred and non-limiting embodiment. As can be seen in FIG. 2, the restroom appliance 117 includes an actuator 203. The actuator 203 may be, for example, a push button, a capacitance sensor, a lever, an infrared sensor, and/or any other like mechanism for requesting a valve operation. The actuator 203 is in communication with the controller 124 associated with the restroom appliance 117 and/or a central controller (not shown in FIG. 2). In the example shown in FIG. 2, the restroom appliance 117 is a toilet and the actuator 203 is used to request a flush. The restroom appliance 117 also includes one or more visual indicators 205, such as a display screen, light emitting diode (LED), and/or the like. In the example shown in FIG. 2, the actuator 203 includes the indicator 205. However, it will be appreciated that indicator(s) 205 may be arranged on or off the restroom appliance 117 at any suitable location such that a prospective user of the restroom appliance 117 is able to view it. For example, one or more indicators 205 may be arranged on the side of the restroom appliance 117, adjacent the actuator 203, or on a wall adjacent the restroom appliance 117.

It will be appreciated that, in other non-limiting embodiments, non-visual indicators may be used, such as audible alarms or tactile feedback. As an example, a non-visual indicator may be a speaker in communication with a controller 124 to provide one or more audible indications to a user. A first audible state, indicating that the restroom appliance 117 has not been recently used, may be the absence of any audible sound. A second audible state, indicating that the restroom appliance 117 has been used within a predetermined time period, may be, for example, a tone such as a "beep" or "click." The audible indication may be presented as a pattern of tones to indicate a number of uses that have already occurred or a number of uses that are left before lockout. For example, the second audible state may be a repeating pattern of two "beeps" or other tones, followed by a pause, and a next audible state may be a repeating pattern of a single "beep" or other tone. A lockout audible state may be an alarm, a continuous tone, a rapid succession of "beeps," and/or the like. The audible states may also be distinguished based on a change in volume, tone, pitch, and/or the like. For example, a different tone may be used for different audible states. It will be appreciated that various other sound and/or tonal patterns may be used.

With continued reference to FIG. 2, the controller 124 may be programmed or configured to permit only a maximum number of valve operations within a given time period. For example, the controller 124 may maintain one or more programmatic counters and timers and permit three valve operations within five minutes. After the maximum number of valve operations has been reached, the controller 124 may prevent further valve operations when requested through use of the actuator 203. In one example, the controller 124 may prevent further activation of the valve 116 until the time period elapses (e.g., five minutes from the first use when a first timer is initiated). In another example, the controller 124 may, in response to reaching the maximum number of valve operations during the time period, prevent further valve operations for an additional lockout time period (e.g., a second time period). Thus, instead of only preventing further use of the valve 116 until the first time period elapses, the controller 124 may, in response to reaching the maximum number of valve operations, initiate a second timer during which additional valve operations are not permitted.

Still referring to FIG. 2, the controller 124 may prevent additional usage of the valve by not responding to requests received through the actuator 203 once the maximum number of uses has been reached. Thus, when the actuator 203 is used to request a valve operation, the controller 124 may determine if a timer is currently operating. If not, the controller 124 can begin a first timer, initiate a counter and set it to 1, and cause the requested valve operation. If an initial timer is currently operating when a request is received, the controller 124 can then determine if the counter has reached the maximum number of uses (e.g., if the counter value is equal to the maximum number of valve operations). If the maximum number of uses has not been reached, the counter is incremented and the controller 124 sends a command to the valve 116 to cause the requested valve operation.

In a preferred and non-limiting embodiment, the visual indicator 205 is configured to display at least three different visual states. As used herein, the terms "first visual state," "second visual state," "third visual state," "fourth visual state," etc., refer to different visual states that may be displayed in any order. The numbering of the visual state does not mean that it is necessarily displayed in that order. A first visual state may be a baseline state in which the restroom appliance may be used. The first visual state may indicate that a maximum number of valve operations are available for the user of the restroom appliance (e.g., that the restroom appliance has not been used by another within a certain time period). As an example, the first visual state may be a steady green light. As another example, the first visual state may be a static state with no further indication provided, such as no light being displayed. A second visual state may indicate that one or more valve operations have already been performed but that the maximum number of uses have not yet been reached. In other words, the second visual state may indicate to a user that the maximum number of uses are no longer available without waiting additional time, but at least one use is still available. For example, if the maximum number of uses is three, the second visual state may be displayed after the first use or after the second use. The second visual state may be, for example, a flashing green or red light.

A third (or fourth, fifth, etc., depending on the maximum number of valve operations) visual state may be a lockout state that indicates that additional valve operations will not be permitted. The third visual state may be, for example, a steady red light. It will be appreciated that numerous different visual states may be used and that the visual states may include any pattern of steady, flashing, and/or different colored lights. Further, the different visual states may also be textually displayed on a display screen, an icon displayed on a display screen, and/or the like. In yet another example, there may be separate indicators for each visual state, such as an array of LEDs where a different LED is lit with each valve operation until the maximum number of valve operations is reached. As used herein, a flashing light refers to a light that repeatedly turns on and off, or repeatedly changes color, at any time interval. For example, a flashing light may be a light that is turned on for a first time period, turned off for a second time period, and then repeats the pattern.

In a preferred and non-limiting embodiment, additional visual states may be presented prior to the lockout state. For example, the visual states may indicate how many uses have already been requested or how many uses are left. For example, if the maximum number of valve operations is three, a second visual state may be displayed in response to the first valve operation or request indicating that two additional valve operations are available within the time period. This visual state may be, for example, a red light that flashes twice, pauses, and continues to flash twice between pauses. After a second valve operation, the next visual state may be, for example, a red light that flashes once between pauses to indicate that only a single valve operation is available.

Figure 3A:
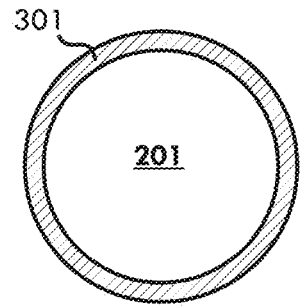
FIGS. 3A and 3B are schematic diagrams for actuators for use in a system for preventing repeated use of a restroom appliance with visual feedback according to the principles of the present invention.
Figure 3B:
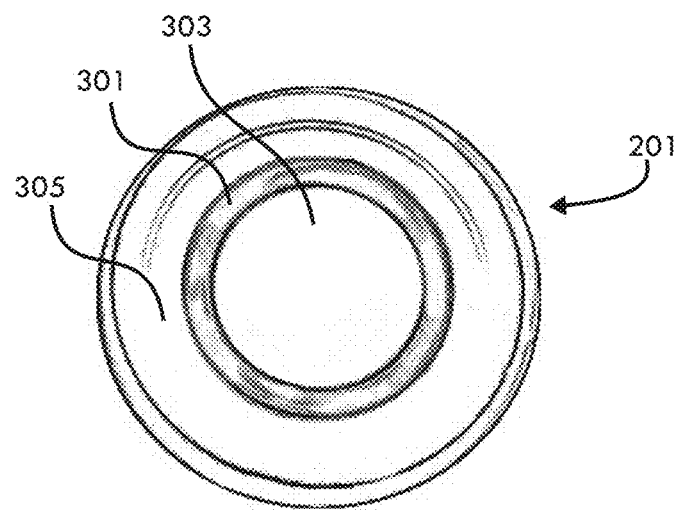

Referring now to FIGS. 3A and 3B, an actuator 201 is shown according to preferred and non-limiting embodiments. Referring specifically to FIG. 3A, the actuator 201 is a push button or a capacitance sensor and is surrounded by an indicator 301. The indicator 301 in this example is a ring that surrounds the actuator 201 and is capable of displaying multiple visual states including, for example, different colors and/or different lighting patterns. The indicator 301 may include one or more LEDs and/or other lighting devices. Referring to FIG. 3B, the actuator 201 is shown to include an indicator 301, a push button 303, and an outer rim 305. The outer rim 305 may be any suitable material, such as stainless steel, plastic, and/or the like. The push button 303 physically depresses upon user actuation, closing a switch that underlies the actuator 201. In other examples, the actuator 201 may be transparent or translucent and the indicator 301 may be positioned behind it such that the actuator 201 and indicator 301 are integrated. Various other arrangements are possible.

Figure 4:
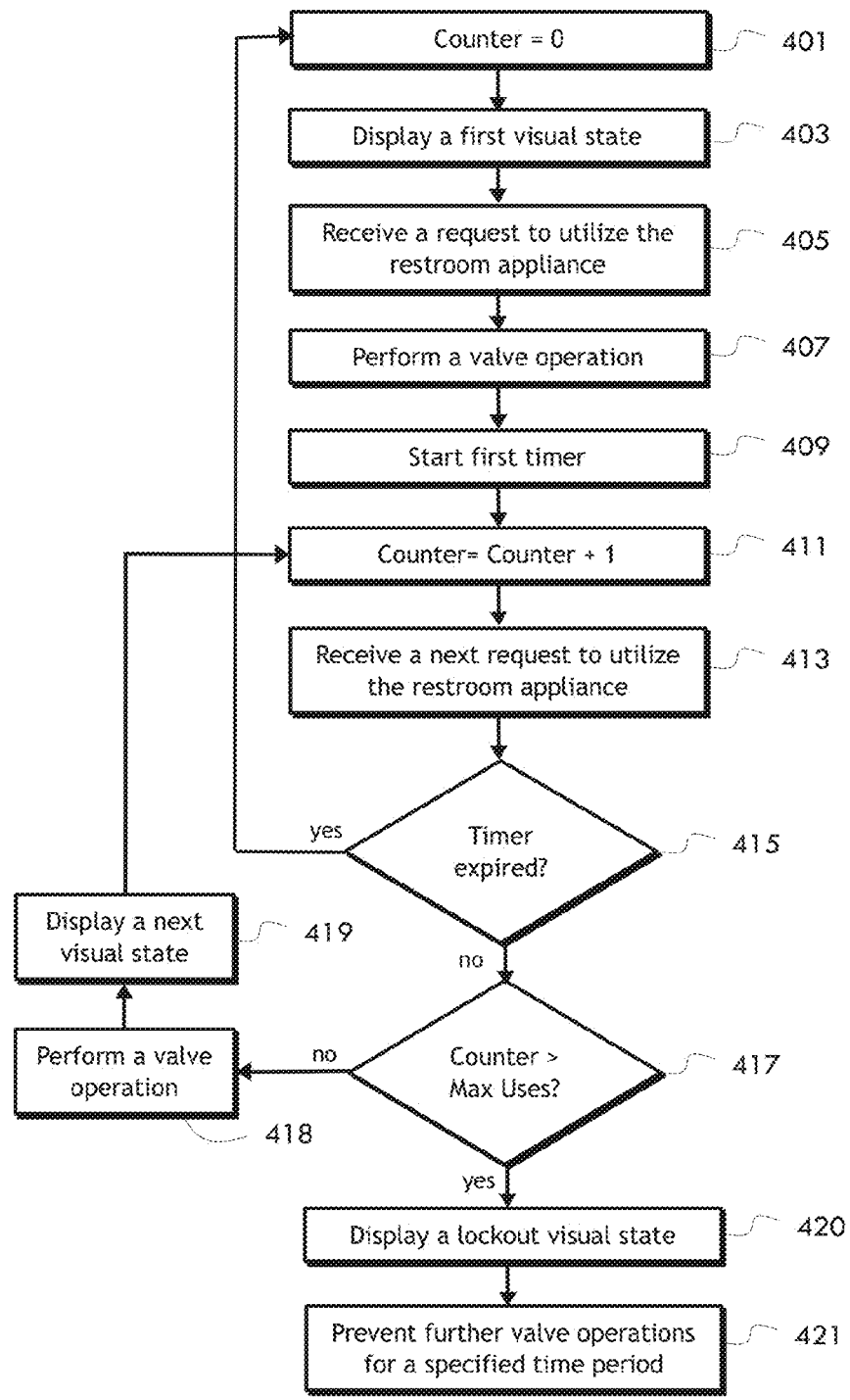
FIG. 4 is a flow diagram for a method for preventing repeated use of a restroom appliance with visual feedback according to the principles of the present invention.

Referring now to FIG. 4, a method for preventing repeated use of a restroom appliance with visual feedback is shown according to a preferred and non-limiting embodiment. At a first step 401, a programmatic counter is initiated and set to zero (0). At step 403, a first visual state is displayed by the visual indicator(s) to indicate to a user that the maximum number of valve operations are available. At step 405, a request is received to utilize the restroom appliance. For example, a user may use an actuator to request a valve operation. The requested valve operation is performed at step 407 and a timer is started at step 409. In a preferred and non-limiting example, the timer is set for 5 minutes, although various other times may be used. At step 411, the counter is incremented. At step 413, a next request to utilize the restroom appliance is received. In response to receiving this next request, it is determined if the first timer has expired at step 415. If the first timer has expired, the method proceeds back to step 401 and the counter is reset, such that the maximum number of valve operations are available. If the timer has not expired, the method proceeds to step 417 and it is determined if the counter has reached the maximum number of valve operations. If the maximum number of valve operations has not been reached, the method proceeds to step 418 in which another valve operation is performed and then to step 419 in which a next visual state is displayed. As an example, the next visual state may be a second, third, fourth, or further visual state, depending on the value of the counter and/or number of requests. The method then goes back to step 411 in which the counter is incremented. If the maximum number of valve operations have been reached, however, the method proceeds from step 417 to step 420, in which a lockout visual state is displayed (e.g., a third, fourth, or further visual state), and then to step 421, in which further valve operations are prevented for a time period (e.g., either the remaining duration of the first time period or the duration of a second time period).

Figure 5:
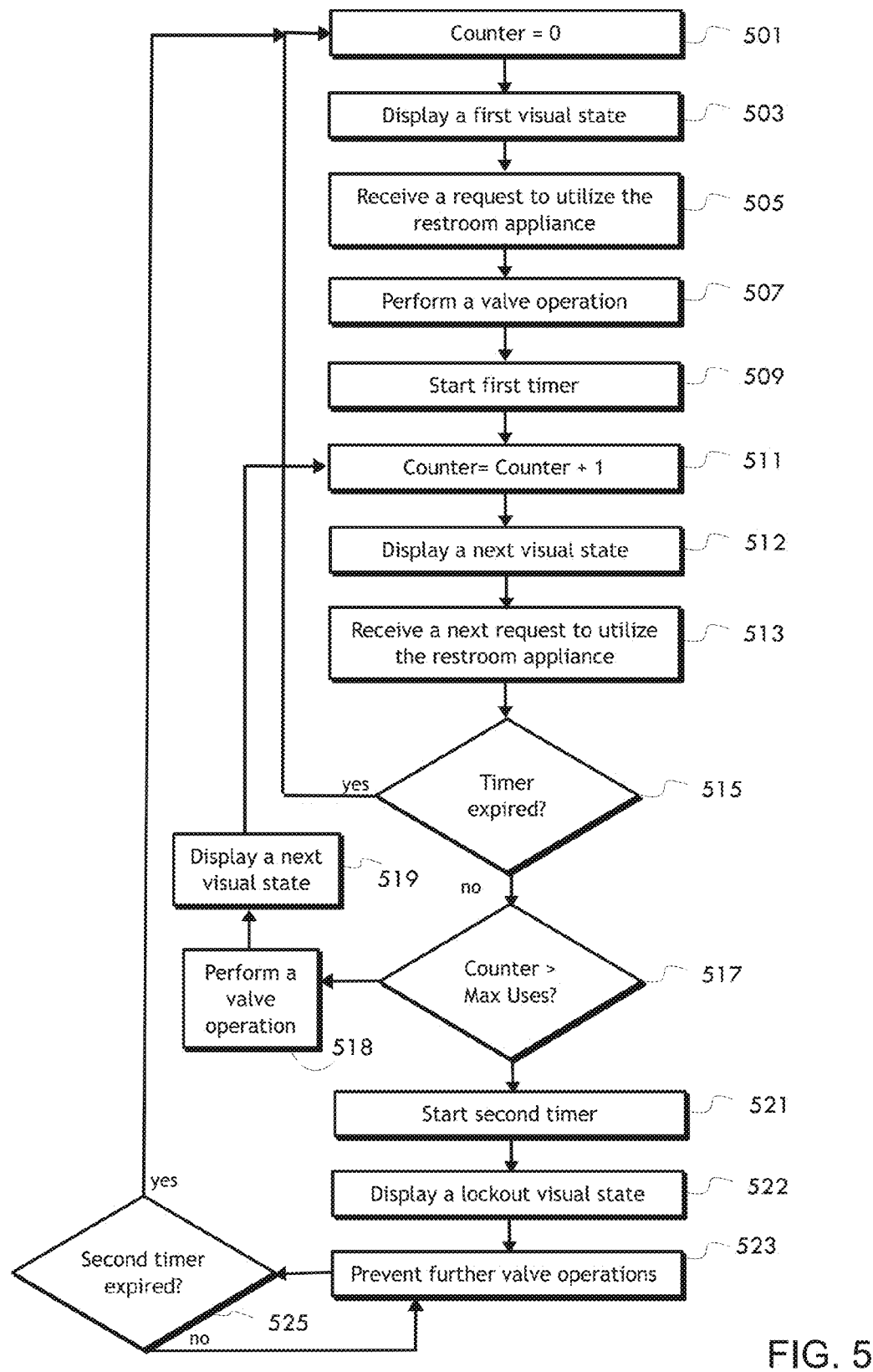
FIG. 5 is a flow diagram for a further method for preventing repeated use of a restroom appliance with visual feedback according to the principles of the present invention.

Referring now to FIG. 5, a method for preventing repeated use of a restroom appliance with visual feedback is shown according to another preferred and non-limiting embodiment. The first several steps are similar to those shown in FIG. 4. At a first step 501, a programmatic counter is initiated and set to zero (0). At step 503, a first visual state is displayed by the visual indicator(s) to indicate to a user that the maximum number of valve operations are available. At step 505, a request is received to utilize the restroom appliance. For example, a user may activate an actuator to cause a valve operation. The requested valve operation is performed at step 507 and a first timer is started at step 509. At step 511, the counter is incremented. At step 513, a next request to utilize the restroom appliance is received. In response to receiving this next request, it is determined if the first timer has expired at step 515. If the timer has expired, the method proceeds back to step 501 and the counter is reset, such that the maximum number of valve operations are available. If the timer has not expired, the method proceeds to step 517 and it is determined if the counter has reached the maximum number of valve operations. If the maximum number of valve operations have not been reached, the method proceeds to step 518 in which another valve operation is performed and then to step 519 in which a next visual state is displayed. As an example, the next visual state may be a second, third, fourth, or further visual state, depending on the value of the counter and/or number of requests. The method then goes back to step 511 in which the counter is incremented. If the maximum number of valve operations have been reached, however, the method proceeds to step 521, in which a second timer is started for a second time period (e.g., a lockout period), then to step 522, in which a lockout visual state is displayed (e.g., a third, fourth, or further visual state), and finally to step 523, in which further valve operations are prevented for the second time period. At step 525 it is determined whether the second time period has elapsed. Once the second time period elapses, the method returns to step 501 and the counter is reset.

Figure 6:
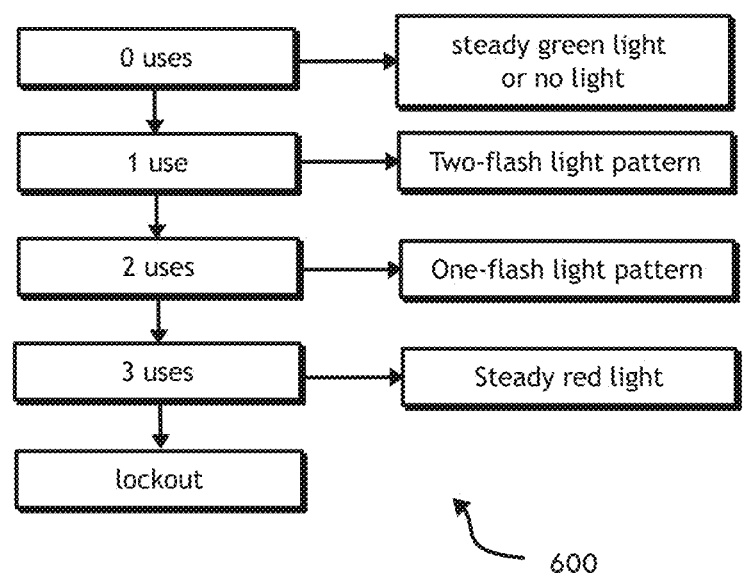
FIG. 6 is a state diagram for a system for preventing repeated use of a restroom appliance with visual feedback according to the principles of the present invention.

Referring now to FIG. 6, a state diagram 600 is shown according to a preferred and non-limiting embodiment. The state diagram 600 shows example visual states that are displayed in response to a number of uses of a restroom appliance. The diagram 600 in FIG. 6 assumes that the maximum number of uses within the time period is three. It will be appreciated that various other maximum values may be used and that any number of different visual states may also be used. For example, at zero uses, the visual state (e.g., a first visual state) may be a steady green light. After one use, the visual state (e.g., a second visual state) may be a two-flash light pattern in which a red or green light flashes twice, pauses, and continues to flash twice to indicate that two uses remain. After two uses, the visual state (e.g., a third visual state) may be a one-flash light pattern in which a red or green light flashes once between pauses to indicate that one use remains. After three uses, the valve enters a lockout status and the visual state (e.g., a fourth visual state) may be a steady red light, a rapidly flashing light, or no light at all.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The invention claimed is:

1. A system for preventing repeated use of a restroom appliance with visual feedback, comprising:
    a valve configured to control flow of a fluid to a restroom appliance by at least one valve operation;
    an actuator configured to request a use of the restroom appliance;
    at least one indicator configured to display at least three different visual states; and at least one controller in communication with the actuator, the valve, and the at least one indicator, the at least one controller programmed or configured to:
  control the at least one indicator to display a first visual state of the at least three different visual states;
  receive, from the actuator during a first time period, a plurality of requests to operate the restroom appliance, the plurality of requests exceeding a maximum number of valve operations associated with the first time period;
  perform a first valve operation in response to receiving a first request of the plurality of requests;
  control the at least one indicator to display a second visual state of the at least three different visual states in response to performing the first valve operation or receiving the first request;
  perform at least one subsequent valve operation in response to receiving a subsequent request of the plurality of requests, the subsequent request corresponding to the maximum number of valve operations;
  control the at least one indicator to display a third visual state of the at least three different visual states in response to performing the at least one subsequent valve operation or receiving the at least one subsequent request; and
  prevent additional valve operations by request of the actuator during a remainder of the first time period and/or for a second time period in response to performing the at least one subsequent valve operation or receiving the at least one subsequent request.

2. The system of claim 1, wherein the at least one controller is further programmed or configured to control the at least one indicator to display the first visual state of the at least three different visual states in response to determining that the first time period and/or the second time period has elapsed.

3. The system of claim 1, wherein the actuator comprises a button comprising the at least one indicator, the at least one indicator configured to display at least two different colored lights.

4. The system of claim 1, wherein the actuator comprises a button comprising the at least one indicator, the at least one indicator arranged as a ring surrounding the button.

5. The system of claim 1, wherein the actuator comprises at least one of the following: an infrared sensor, a proximity sensor, a push button, a capacitance sensor, a lever, or any combination thereof.

6. The system of claim 1, wherein the first visual state is a steady light, wherein the second visual state is a flashing light, and wherein the third visual state is a steady or flashing light of a different color than the first visual state.

7. The system of claim 1, wherein the maximum number of valve operations is three.

8. The system of claim 1, wherein the second state comprises a light pattern indicating a number of uses that have taken place or a number of valve operations that are left within the first time period.

9. The system of claim 8, wherein the light pattern comprises flashing a light a number of times corresponding to the number of valve operations that are left within the first time period.

10. The system of claim 1, wherein additional valve operations by request of the actuator are prevented for a second time period in response to performing the at least one subsequent valve operation or receiving the at least one subsequent request, the second time period comprising a lockout period.

11. The system of claim 1, wherein additional valve operations by request of the actuator are prevented for a remaining duration of the first time period in response to performing the at least one subsequent valve operation or receiving the at least one subsequent request.

12. The system of claim 1, wherein the first valve operation and the at least one subsequent valve operation comprise at least one of the following: a flush of a flush valve, opening a faucet valve for a predetermined time period, or opening a shower valve for a predetermined time period.

13. A method for preventing repeated use of a restroom appliance with visual feedback, the restroom appliance comprising a valve and an actuator configured to cause an operation of the valve, the method comprising:
  controlling at least one indicator to display a first visual state of at least three different visual states;
  receiving, from the actuator during a first time period, a plurality of requests to operate the restroom appliance, the plurality of requests exceeding a maximum number of valve operations associated with the first time period;
  performing a first valve operation in response to receiving a first request of the plurality of requests;
  controlling the at least one indicator to display a second visual state of the at least three different visual states in response to performing the first valve operation or receiving the first request;
  performing at least one subsequent valve operation in response to receiving a subsequent request of the plurality of requests, the subsequent request corresponding to the maximum number of valve operations;
  controlling the at least one indicator to display a third visual state of the at least three different visual states in response to performing the at least one subsequent valve operation or receiving the at least one subsequent request; and
  preventing additional valve operations by request of the actuator during a remainder of the first time period and/or for a second time period in response to performing the at least one subsequent valve operation or receiving the at least one subsequent request.

14. The method of claim 13, further comprising controlling the at least one indicator to display the first visual state of the at least three different visual states in response to determining that the first time period and/or the second time period has expired.

15. The method of claim 13, wherein the actuator comprises a button comprising the at least one indicator.

16. The method of claim 13, wherein the actuator comprises a button comprising the at least one indicator, the at least one indicator arranged as a ring surrounding the button.

17. The method of claim 13, wherein the actuator comprises at least one of the following: an infrared sensor, a proximity sensor, a button, a lever, or any combination thereof.

18. The method of claim 13, wherein the first visual state is a steady light, wherein the second visual state is a flashing light, and wherein the third visual state is a steady or flashing light of a different color than the first visual state.

19. The method of claim 13, wherein the maximum number of valve operations is three, and wherein the first time period is about five minutes.

20. The method of claim 13, wherein the at least one indicator comprises a first light of a first color and a second light of a second color.

21. The method of claim 13, wherein the second state comprises a light pattern indicating a number of uses that have taken place or a number of uses that are left within the first time period.

22. The method of claim 21, wherein the light pattern comprises repeatedly flashing a light a number of times corresponding to the number of uses that have taken place or the number of uses that are left within the first time period.

23. The method of claim 13, wherein a fourth visual state displayed after the second visual state and before the third visual state comprises a light pattern comprising flashing a light once between repeating intervals.

24. The method of claim 13, wherein the first valve operation and the at least one subsequent valve operation comprise at least one of the following: a flush of a flush valve, opening a faucet valve for a predetermined time period, opening a shower valve for a predetermined time period, or any combination thereof.

25. An apparatus for preventing a user from repeatedly using a restroom appliance, the restroom appliance comprising a valve and an actuator configured to cause an operation of the valve, the apparatus comprising at least one controller in communication with the valve and the actuator, the at least one controller programmed or configured to:

control at least one indicator to display a first visual state of the at least three different visual states;

receive, from the actuator during a first time period, a plurality of requests to operate the restroom appliance, the plurality of requests exceeding a maximum number of valve operations associated with the first time period;

perform a first valve operation in response to receiving a first request of the plurality of requests;

control the at least one indicator to display a second visual state of at least three different visual states in response to performing the first valve operation or receiving the first request;

perform at least one subsequent valve operation in response to receiving a subsequent request of the plurality of requests, the subsequent request corresponding to the maximum number of valve operations;

control the at least one indicator to display a third visual state of the at least three different visual states in response to performing the at least one subsequent valve operation or receiving the at least one subsequent request; and prevent additional valve operations by request of the actuator during the first time period and/or for a second time period in response to performing the at least one subsequent valve operation or receiving the at least one subsequent request.

* * * * *

UNITED STATES PATENT AND TRADEMARK OFFICE
CERTIFICATE OF CORRECTION

PATENT NO. : 9,963,863 B2
APPLICATION NO. : 15/259723
DATED : May 8, 2018
INVENTOR(S) : Rock R. Allard, III It is certified that error appears in the above-identified patent and that said Letters Patent is hereby corrected as shown below:

On the Title Page

Column 1, Line 2, delete "AND PREVENTING" and insert -- FOR PREVENTING --

In the Specification

Column 1, Line 2, delete "AND PREVENTING" and insert -- FOR PREVENTING --

Signed and Sealed this
Fourteenth Day of August, 2018

Andrei Iancu
*Director of the United States Patent and Trademark Office*